United States Patent [19]

Cheung et al.

[11] Patent Number: 4,594,341

[45] Date of Patent: Jun. 10, 1986

[54] PERHYDRO-1,4-THIAZEPIN-5-ONE AND PERHYDRO-1,4-THIAZOCIN-5-ONE DERIVATIVES AS ANTIHYPERTENSIVES

[75] Inventors: Yak-Fa Cheung, Westfield; Eugene D. Thorsett, Fanwood; Arthur A. Patchett, Westfield, all of N.J.

[73] Assignee: Merck & Co., Inc., Rahway, N.J.

[21] Appl. No.: 728,132

[22] Filed: Apr. 29, 1985

Related U.S. Application Data

[63] Continuation-in-part of Ser. No. 364,481, Apr. 6, 1982, abandoned, which is a continuation-in-part of Ser. No. 270,756, Jun. 5, 1981, abandoned.

[51] Int. Cl.[4] .................. A61K 31/55; A61K 31/395; C07D 281/00; C07D 281/18

[52] U.S. Cl. ..................... 514/211; 260/239.3 R; 514/183

[58] Field of Search ................ 260/239.3 R; 514/211, 514/183

[56] References Cited

U.S. PATENT DOCUMENTS 4,409,146 10/1983 Thorsett et al. ............. 260/239.3 R Primary Examiner—Robert T. Bond
Attorney, Agent, or Firm—Salvatore C. Mitri; Michael C. Sudol

[57] ABSTRACT

There are disclosed perhydro-1,4-thiazepin-5-one and perhydro-1,4-thiazocin-5-one derivatives and related compounds which are useful as angiotensin converting enzyme inhibitors and as antihypertensives.

20 Claims, No Drawings

PERHYDRO-1,4-THIAZEPIN-5-ONE AND PERHYDRO-1,4-THIAZOCIN-5-ONE DERIVATIVES AS ANTIHYPERTENSIVES

BACKGROUND OF INVENTION

This is a continuation-in-part of application Ser. No. 364,481 filed Apr. 6, 1982 now abandoned, which, in turn, is a continuation-in-part of application Ser. No. 270,756 filed June 5, 1981, now abandoned.

This invention relates to perhydro-1,4-thiazepin-5-one and perhydro-1,4-thiazocin-5-one derivatives and related compounds which are useful as angiotensin converting enzyme inhibitors and as antihypertensives. The compounds of this invention are represented by the following formula:

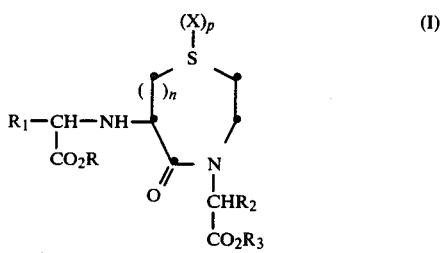

wherein:

R and $R_3$ are independently hydrogen, $C_1$–$C_6$ alkyl, aryl, and aralkyl;

$R_1$ is hydrogen; hydrocarbon of from 1 to 12 carbon atoms which include branched, cyclic and unsaturated hydrocarbon groups (such as 3-methyl-1-butyl, 2-cyclohexylethyl, 3,3-dimethylallyl, and the like); substituted $C_1$–$C_6$ alkyl wherein the substituent can be halo, hydroxy, carboxy, lower alkylthio, lower alkoxy, lower alkoxy carbonyl, lower aralkoxy carbonyl, amino, lower alkylamino, diloweralkylamino, or acylamino; substituted $C_1$–$C_6$ alkyl having the formula $R_A(CH_2)_n$—Q—$(CH_2)_m$ wherein n is 0–2, m is 1–3, $R_A$ is aryl or heteroaryl optionally substituted by amino, diloweralkylamino, lower alkylamino, hydroxy, hydroxy loweralkyl, aminoloweralkyl, trihaloloweralkyl, cyano, nitro, sulfonamide, aroyl, lower alkyl, halo, dihalo, and lower alkoxy, and Q is O, S, N—$R_B$, CONR$_C$, NR$_C$CO, CH=CH wherein $R_B$ is hydrogen, loweralkyl, aryl, aralkyl, lower alkanoyl, or aroyl, and $R_C$ is hydrogen or lower alkyl; aryl; substituted aryl wherein the substituent is lower alkyl, amino loweralkyl, loweralkoxy, aryloxy, aroyl, hydroxy, halo, or dihalo; aralkyl or heteroaralkyl which include branched lower alkyl groups (such as 2,2-dibenzylethyl); substituted aralkyl or substituted heteroaralkyl which include branched lower alkyl groups wherein the lower alkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, amino lower alkyl, lower alkanoylamino, aroylamino, diloweralkylamino, lower alkylamino, hydroxy loweralkyl, trihalo loweralkyl, nitro, cyano, or sulfonamido;

$R_2$ is hydrogen or loweralkyl;

n is 1 or 2;

p is 0 or 1;

X is oxygen; and, the pharmaceutically acceptable salts thereof.

The lower alkyl groups, except where noted otherwise, represented by any of the variables include straight, branched and unsaturated chain hydrocarbon radicals from one to six carbon atoms, for example, methyl, ethyl, propyl, isopropyl, butyl, isobutyl, t-butyl, pentyl, isopentyl, hexyl or vinyl, allyl, butenyl and the like.

The aralkyl and heteroaralkyl groups represented by any of the above variables have from one to six carbon atoms in the alkyl portion thereof and include, for example, benzyl, phenethyl, 3,3-diphenylpropyl, 3-indolylmethyl, and the like.

Halo means chloro, bromo, iodo or fluoro.

Aryl where it appears in any of the radicals, except where noted, represents phenyl, naphthyl, or biphenyl.

Aroyl includes benzoyl, 1-naphthoyl, and the like.

Heteroaryl includes, for example, indolyl, thienyl, imidazolyl, furyl, benzimidazolyl, pyridyl, quinolinyl, isoquinolinyl, and benzothienyl.

Acylamino refers to lower alkanoylamino and aroylamino groups such as, for example, acetylamino, benzoylamino, and the like.

Preferred are those compounds of Formula I wherein:

R and $R_3$ are hydrogen, loweralkyl, aryl or aralkyl;

$R_1$ is hydrocarbon of 1–10 carbon atoms which include branched, cyclic and unsaturated hydrocarbon groups; substituted loweralkyl wherein the substituent can be hydroxy, lower alkylthio, amino, alkylamino, diloweralkylamino, and acylamino; substituted lower alkyl having the formula $R_A(CH_2)_n$—Q—$(CH_2)_m$— wherein n is 0–2, m is 1–3, $R_A$ is aryl or heteroaryl optionally substituted by alkyl, halo, dihalo, amino, cyano, hydroxy, or alkoxy, and Q is O, S, N—$R_B$, CONR$_C$, NR$_C$CO, or CH=CH wherein $R_B$ is hydrogen, lower alkyl, aralkyl, lower alkanoyl, or aroyl and $R_C$ is hydrogen or lower alkyl; aralkyl or heteroaralkyl which include branched lower alkyl groups; substituted aralkyl or substituted heteroaralkyl which include branched lower alkyl groups wherein the lower alkyl substituents can be amino, acylamino, or hydroxy and the aryl and heteroaryl substituents can be lower alkyl, halo, dihalo, amino, cyano, hydroxy, lower alkoxy, amino loweralkyl, or hydroxyloweralkyl;

$R_2$ is hydrogen or lower alkyl;

n is 1 or 2; and, p is 0.

More preferred are those compounds of Formula I wherein:

R, $R_1$ and $R_2$ are as defined above, n is 1, and p is 0.

Most preferred are those compounds of Formula I wherein:

R and $R_3$ are independently hydrogen, lower alkyl of 1 to 4 carbon atoms, phenyl, or benzyl;

$R_1$ is alkyl of 1–8 carbon atoms which include branched alkyl groups; substituted lower alkyl wherein the substituent can be amino or loweralkylthio; substituted lower alkyl having the formula $R_A(CH_2)_n$—Q—$(CH_2)_m$— wherein n is O, m is 1, $R_A$ is phenyl, and Q is O or S; aralkyl wherein the aryl is phenyl or naphthyl and the alkyl group contains 1 to 3 carbon atoms, or heteroaralkyl wherein the heteroaryl group is indole, thiophene, imidazole, pyridine, quinoline or isoquinoline and the alkyl group contains 1 to 3 carbon atoms; substituted aralkyl wherein the aryl is a phenyl group, the alkyl contains 1 to 3 carbon atoms, and the phenyl substituents can be halo, hydroxy, phenoxy, lower alkoxy, amino, or aminomethyl;

$R_2$ is hydrogen or lower alkyl;

n is 1; and, p is 0.

The preferred, more preferred and most preferred compounds also include the pharmaceutically acceptable salts thereof.

The products of Formula I and the preferred subgroups thereof can be produced by the methods depicted in the following Reaction Scheme wherein R, $R_1$, $R_2$, $R_3$, X, p and n are as defined above.

As will be evident to those skilled in the art and as demonstrated in the Examples, reactive groups not involved in the condensations, such as amino, carboxy, hydroxy, etc., may be protected by methods standard in peptide chemistry prior to the coupling reactions and subsequently deprotected to obtain the desired products.

REACTION SCHEME

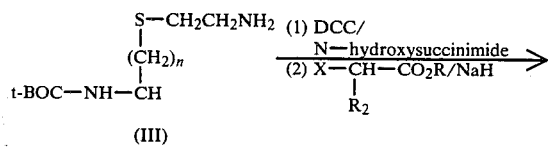

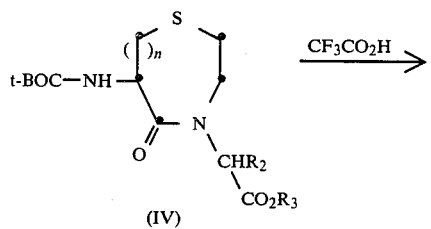

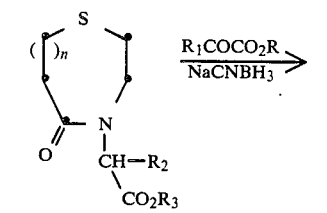

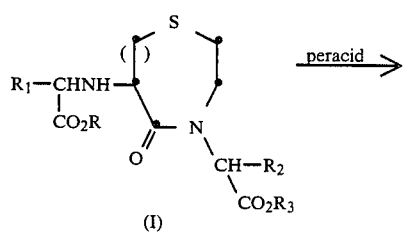

-continued
REACTION SCHEME

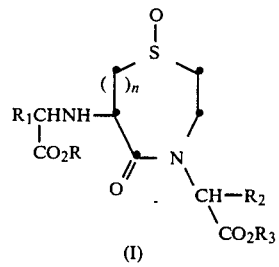

With reference to the Reaction Scheme, the α-t-BOC derivatives of S-(aminoethyl)cysteine and of S-(aminoethyl)homocysteine (II) are liberated from their corresponding S-(carbobenzyloxyaminoethyl) precursors using sodium and liquid ammonia. They are then cyclized to thialactams via carboxyl activating reagents such as dicyclohexylcarbodiimide in the presence of N-hydroxysuccinimide. N-Alkylation of these lactams with α-haloesters or α-haloacids in the presence of a base such as sodium hydride affords, after chromatography, the lactam intermediate IV. The tertiary butoxycarbonyl group can be removed from compound IV under standard acid conditions to afford the aminothialactam derivative V. Reductive condensation of the latter with α-ketoacids or α-ketoesters in the presence of sodium cyanoborohydride yields compounds of Formula I. These, in turn, can be converted to sulfoxides by oxidation with a peracid such as m-chloroperbenzoic acid. By a suitable choice of R groups, compounds of Formula I as free diacids, monoesters and diesters are formed. Protecting groups of optional amino functions in the $R_1$ group may be utilized and removed by methods which are standard in peptide chemistry.

The reductive alkylation of α-ketoacids or α-ketoesters with compound V generates a new assymmetric center which is preferred in the S configuration. When $R_2$ is lower alkyl, an additional asymmetric center is present in compounds of Formula I. The preferred conformation of this ester is S although the R conformation is also consistent with good activity. The preferred conformation at the carbon bearing the alkylated amino function in Formula I is that corresponding to a natural L-amino acid. Mixtures of diastereomers of these compounds have activity and may be utilized in the treatment of hypertension. Alternatively, the preferred diastereomer may be isolated by liquid chromatography.

The α-ketocarboxylate derivatives used in the reductive alkylation can include such compounds as, for example ethyl 2-oxo-4-phenylbutyrate, ethyl 4-p-chlorophenyl-2-oxobutyrate, ethyl 4-(imidazolyl)-2-oxobutyrate, ethyl 2-oxo-4-(2-thienyl)-butyrate, ethyl 2-oxo-4-(2-napthyl)-butyrate, ethyl 4-p-hydroxyphenyl-2-oxobutyrate, ethyl phenoxypyruvate, ethyl 2-oxo-5-phenylpentanoate, ethyl 4-p-methoxyphenyl-2-oxobutyrate, ethyl 5-methyl-2-oxohexanoate, benzyl 2-oxo-6-phthalimidohexanoate, and the like, and their respective free acids.

The starting materials which are required for the above processes herein described are known in the literature or can be made by known methods from known starting materials.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like. Also salts with organic and inorganic acids may be prepared, e.g., HCl, HBr, $H_2SO_4$, $H_3PO_4$, methanesulfonic, toluensulfonic, maleic, fumaric, camphorsulfonic. The non-toxic physiologically acceptable salts are preferred, although other salts are also useful, e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A, Reinharz and M. Roth, *Biochem. Biophys. Acta,* 206, 136 (1970) in which the hydrolysis of carbobenzyloxy-phenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.,* 104, 646 (1960) or in a high renin rat model such as that of S. Koletsky et al., *Proc. Soc. Exp. Biol. Med.* 125, 96 (1967).

Thus, the compounds of this invention are useful as antihypertensives in treating hypertensive mammals, including humans, and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage range of 2 to 200 mg per patient generally given several times, thus giving a total daily dose of from 2 to 800 mg per day. The dose will vary depending on severity of disease, weight of patient and other factors which a person skilled in the art will recognize.

Also, the compounds of this invention may be given in combination with other diuretics or antihypertensives. Typically these are combinations whose individual per day dosages range from one-fifth of the minimally recommended clinical dosages to the maximum recommended levels for the entities when they are given singly. To illustrate these combinations, one of the antihypertensives of this invention effective clinically in the range 5-200 milligrams per day can be effectively combined at levels ranging from 1-200 milligrams per day with the following antihypertensives and diuretics in dose ranges per day as indicated:

hydrochlorothiazide (10-100 mg), timolol (5-60 mg), methyldopa (65-2000 mg), the pivaloyloxyethyl ester of methyldopa (30-1000 mg),indacrinone and variable ratios of its enantiomers (25-150 mg), and (+)-4-{3-{[2-(1-hydroxycyclohexyl)ethyl]-4-oxo-2-thiazolidinyl} propyl}benzoic acid (10-100 mg).

In addition, the triple drug combinations of hydrochlorothiazide (10-100 mg) plus amiloride (5-20 mg) plus converting enzyme inhibitor of this invention (1-200 mg) or hydrochlorothiazide (10-100 mg) plus timolol (5-60 mg) plus the converting enzyme inhibitor of this invention (1-200 mg) are effective combinations to control blood pressure in hypertensive patients.

The above dose ranges will be adjusted to a unit basis as necessary to permit divided daily dosage.

Typically, the combinations shown above are formulated into pharmaceutical compositions as discussed below.

About 1 to 100 mg of a compound or mixture of compounds of Formula I or physiologically acceptable salts thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by column chromatography or fractional crystallization. Unless otherwise indicated, all temperatures are given in degrees Celsius and nmr resonances are given in ppm downfield from the TMS resonance.

EXAMPLE 1

N-t-Butoxycarbonyl-S-(2-carbobenzyloxyaminoethyl)-L-cysteine

S-(2-Carbobenzyloxyaminoethyl)-L-cysteine (0.6 g) in 6 ml of 2:1 dioxane-water and 2 ml of 1M sodium hydroxide solution is treated with di-t-butyl dicarbonate (0.48 g) until reaction is complete. After removal of dioxane, excess reagent is extracted into ether. Upon acidification of the aqueous solution to pH 2 with 4M hydrochloric acid, the product separates out as an oil (0.38 g). The NMR spectrum of such a sample shows a broad singlet at 7.6, a singlet at 7.3, a singlet at 5.0, complex multiplets between 2.6 and 3.7, and a singlet at 1.4.

EXAMPLE 2

N-t-Butoxycarbonyl-S-(2-aminoethyl)-L-cysteine

N-t-Butoxycarbonyl-S-(2-carbobenzoxyaminoethyl)-L-cysteine (9.9 g) in 500 ml of liquid ammonia is treated with sodium metal until reaction is complete, as indicated by the persistence of a blue color. Ammonium chloride (1 g) is added, followed by ethanol (50 ml). Excess ammonia is let evaporate away. The residue is dissolved in a minimal amount of water, and extracted with ether. The aqueous layer is again taken to dryness, and the residue extracted with ethanol containing 6 ml of ammonium hydroxide. Upon removal of the ethanol the residue obtained is redissolved in 15 ml of water, and passed through 10 ml of Dowex-50 resin on the ammonium cycle. The resin is washed with 30 ml of water. The product (5.0 g) is obtained upon lyophilization of the eluent. The NMR spectrum (in $D_2O$ and NaOD) of such a sample shows a multiplet at 4.1, complex absorption between 2.6 and 3.0, and a singlet at 1.4.

EXAMPLE 3

6-t-Butoxycarbonylamino-perhydro-1,4-thiazepin-5-one

N-t-Butoxycarbonyl-S-(2-aminoethyl)-L-cysteine (5.0 g) and N-hydroxysuccinimide (2.6 g) are dissolved in 500 ml of DMF. With cooling in an ice-bath, a solution of dicyclohexylcarbodiimide (4.7 g) in 10 ml of DMF is added dropwise over a period of 15 minutes. The reaction mixture is kept in a 4° room for 10 days. The solvent is then removed by lyophilization. The crude product is extracted into chloroform. Repeated chromatography on silica gel (20:1 chloroform-methanol) affords the pure product (3.1 g). The NMR spectrum is consistent with the assigned structure. A pure sample is obtained by recrystallization (ether-methanol) and analyzes for $C_{10}H_{18}N_2O_3S$.

EXAMPLE 4

6-t-Butoxycarbonylamino-4-N-(carbomethoxymethyl)-perhydro-1,4-thiazepin-5-one 6-t-Butoxycarbonylamino-perhydro-1,4-thiazepin-5-one (0.1 g) and methyl iodoacetate (0.1 g) are dissolved in 1 ml of THF. Sodium hydride (50% suspension in oil) is added in batches. After one hour at room temperature, the reaction is quenched with 2 ml of 10% ammonium chloride solution. The crude product is extracted into methylene chloride, and subsequently chromatographed on silica gel (40:1 chloroform-methanol) to yield the pure product (0.09 g). The NMR spectrum is consistent with the assigned structure. A pure sample is obtained by recrystallization from ether-methanol and analyzes for $C_{13}H_{22}N_2O_5S$.

EXAMPLE 5

6-Amino-4-N-(carbomethoxymethyl)-perhydro-1,4-thiazepin-5-one, Trifluoroacetate Salt 6-t-Butoxycarbonylamino-4-N-(carbomethoxymethyl)-perhydro-1,4-thiazepin-5-one (0.53 g) is dissolved in 2 ml of trifluoroacetic acid. At the end of one hour at room temperature the trifluoroacetic acid is removed under vacuum. The residue is partitioned between water and ether. The aqueous layer is washed three more times with ether, and then lyophilized to yield the product as a white solid (0.52 g).

EXAMPLE 6

4-N-(Carbomethoxymethyl)-6-(carboethoxy-3-phenylpropylamino)-perhydro-1,4-thiazepin-5-one 6-Amino-4-N-(carbomethoxymethyl)perhydro-1,4-thiazepin-5-one, trifluoroacetate salt (0.166 g), sodium acetate (0.04 g), and ethyl 2-keto-4-phenylbutyrate are dissolved in 1 ml of methanol. After ½ hour at room temperature, a solution of sodium cyanoborohydride (0.16 g) in 0.5 ml of methanol is added dropwise over a period of one hour. At the end of seven hours, the reaction mixture is partitioned between chloroform and water. The aqueous phase is adjusted to pH 10 with sodium bicarbonate. The organic layer is separated and washed two more times with water. After chromatography on silica gel (1:1 ethyl acetate-hexanes), the product is obtained as an oil (0.17 g). The NMR spectrum shows a singlet at 7.2, complex absorption between 3.7 and 4.4, a multiplet between 3.1 and 3.4, a multiplet between 3.6 and 3.9, a multipet between 1.9 and 2.2, and a triplet at 1.3.

EXAMPLE 7

4-N-(Carboxymethyl)-6-[carboxy-3-phenylpropylamino]-perhydro-1,4-thiazepin-5-one 4-[Carbomethoxymethyl]-6-[carboethoxy-3-phenyl propylamino]-perhydro-1,4-thiazepin-5-one (0.1 g) is dissolved in 1.5 ml of methanol and 0.5 ml of 1M sodium hydroxide. At the end of 4 hours at room temperature, 2 ml of water is added. The resulting solution is loaded onto a column of Dowex-50 resin (on the proton cycle). After thorough washing with water, the column is developed with 5% pyridine. The eluent is lyophilized to yield the product as a white solid (0.085 g). The sample analyzes for $C_{17}H_{23}N_2O_5S \cdot \frac{1}{2}H_2O$.

EXAMPLE 8

6-t-Butoxycarbonylamino-4-N-(1-carbomethoxyethyl)-perhydro-1,4-thiazepin-5-one

The above-named compound is prepared from 6-t-butoxycarbonylamino-perhydro-1,4-thiazepin-5-one (0.1 g) and methyl iodopropionate (0.11 g) according to the procedure described in Example 4. The product (0.11 g) is obtained after chromatography. The NMR spectrum is consistent with the assigned structure.

EXAMPLE 9

6-Amino-4-N-[1-carboxyethyl]perhydro-1,4-thiazepin-5-one 6-t-Butoxycarbonylamino-4-N-[1-carbomethoxyethyl]-perhydro-1,4-thiazepin-5-one (0.11 g) is treated with trifluoroacetic acid and worked up as described in Example 5. The white solid (0.095 g) obtained after lyophilization is dissolved in 2 ml of methanol and 1 ml of 1M sodium hydroxide. At the end of four hours at room temperature, the solution is titrated to pH 7 with 1M hydrochloric acid, and subsequently loaded onto a column of Dowex-50 (on the proton cycle. After thorough washing with water, the column is developed with a 5% pyridine solution. The eluent is lyophilized to afford the product as a white powdery solid (0.05 g). The NMR spectrum (in $D_2O$) shows a multiplet from 4.0 to 4.3, a multiplet from 3.1 to 3.4, a doublet at 1.8 and a doublet at 1.7.

EXAMPLE 10

4-N-(1-carboxyethyl)-6-(1-carboethoxy-3-phenylpropylamino)-perhydro-1,4-thiazepin-5-one 6-Amino-4-N-(1-carboxyethyl)perhydro-1,4-thiazepin-5-one (0.05 g) is suspended in 1 ml of methanol. Ethyl 2-keto-4-phenylbutyrate (0.24 g) and acetic acid (0.02 g) are added. A 1M solution of sodium cyanoborohydride (0.75 ml) is added dropwise over a period of twenty hours. After removal of methanol, the reaction mixture is taken up in water and loaded onto a column of Dowex-50 (on the proton cycle). After thorough washing with water, the column is developed with 5% pyridine solution. Lyophilization of the eluent afforded the crude product (0.08 g), which is purified by preparative thin layer chromatography on silica gel (9:1 chloroform-methanol containing 5% formic acid). The product is obtained as an oil (0.07 g). The NMR spectrum is consistent with the assigned structure.

EXAMPLE 11

4-N-(carbomethoxymethyl)-6-(1-carboethoxy-3-phenylpropylamino)-perhydro-1,4-thiazepin-5-one, 1-S-oxide 4-N-(carbomethoxymethyl)-6-(carboethoxy-3-phenylpropylamino)-perhydro-1,4-thiazepin-5-one (0.04 g) is dissolved in 1 ml of methylene chloride, and the solution cooled in an ice-bath. m-Chloroperbenzoic acid (0.024 g) is added. At the end of one hour, thin layer chromatography on silica gel (10:1 chloroform-methanol) shows completion of reaction. The reaction mixture is washed with saturated sodium bicarbonate solution and water. Usual work-up of the organic layer yielded the crude product as a yellow glass (0.045 g) which is purified by chromatography on silica gel (9:1 chloroform-methanol) to afford a yellow glass (0.04 g). The NMR spectrum is consistent with the assigned structure.

EXAMPLE 12

4-N-(Carboxymethyl)-6-(1-carboxy-3-phenylpropylamino)-perhydro-1,4-thiazepin-5-one, 1-S-oxide 4-N-(carbomethoxymethyl)-6-(carboethoxy-3-phenylpropylamino)-perhydro-1,4-thiazepin-5-one, 1-S-oxide (0.05 g) is dissolved in 1 ml of methanol and 0.3 ml of 1M sodium hydroxide. After four hours at room temperature, 5 ml of water is added an the solution titrated to pH 7 with 1M hydrochloric acid. The solution is loaded on a column of Dowex-50 column (on the proton cycle). After thorough washing with water, the column is developed with 5% pyridine solution. Lyophilization of the eluent afforded the product as a white solid (0.02 g). The NMR spectrum is consistent with the assigned structure.

EXAMPLE 13

N-t-Butoxycarbonyl-D,L-homocysteine thiolactone

D,L-Homocysteine thiolactone, hydrochloride (0.153 g) and triethylamine (0.15 ml) are dissolved in 2 ml of chloroform. Di-t-butyldicarbonate (0.22 g) is added. After ½ hour, the reaction mixture is washed with dilute hydrochloric acid, and saturated sodium chloride solution. Usual work-up of the organic layer afforded the product as a white crystalline solid (0.2 g). The NMR spectrum shows a broad doublet at 5.3, a quintet at 4.3, a multiplet at from 3.2 to 3.5, a complex absorption between 2.0 and 3.0, and a singlet at 1.5.

EXAMPLE 14

N-t-Butoxycarbonyl-S-[2-carbobenzoxyaminoethyl]-D,L-homocysteine

N-t-Butoxycarbonyl-D,L-homocysteine thiolactone (0.22 g) is dissolved in 2 ml each of dioxane and 1M sodium hydroxide. N-carbobenzoxycarbonyl-2-iodoethylamine (0.31 g) is added. After standing over-night at room temperature, the solution is concentrated to remove most of the dioxane. The aqueous solution is acidified with dilute hydrochloric acid, and extracted with methylene chloride. The organic layer is washed with saturated sodium chloride solution and worked up as usual to yield the product as an oil (0.36 g). The NMR spectrum shows a singlet at 7.3, a broad singlet at 6.9, a singlet at 5.1, a multiplet between 4.1 and 4.4, a multiplet between 3.1 and 3.5, a multiplet between 2.5 and 2.8, a multiplet between 1.8 and 2.2, and a singlet at 1.5.

EXAMPLE 15

N-t-Butoxycarbonyl-S-(2-aminoethyl)-D,L-homocysteine

N-t-Butoxycarbonyl-S-(2-carbobenzyloxycarbonyl aminoethyl)-D,L-homocysteine (1.0 g) is treated with sodium in liquid ammonia according to the procedure described in Example 2. After the ammonia has evaporated off, the residue is extracted with ethanol. Inorganic salts (0.4 g) is removed by filtration. After removal of ethanol, the residue is taken up in 5 ml of water. The aqueous solution is extracted with ether, and then acidified to pH 4 with 4M hydrochloric acid. The solution is concentrated to a volume of 2 ml. Excess ether is added. The product crystallizes out as a white solid (0.32 g). The NMR spectrum (in MeOH-$d_4$ and NaOD) shows a triplet at 3.7, complex absorption between 2.1 and 2.6, a multiplet between 1.5 and 1.9, and a singlet at 1.2.

EXAMPLE 16

6-t-butoxycarbonylamino-perhydro-1,4-thiazocin-5-one

N-t-Butoxycarbonyl-S-(2-aminoethyl)-D,L-homocysteine (0.1 g) and hydroxysuccinimide (0.044 g) are dissolved in 4 ml of DMF. Dicyclohexylcarbodiimide (0.086 g) in 1 ml of DMF is added dropwise. After 4 days at room temperature, the reaction mixture is filtered, and then lyophilized. The residue is taken up in methylene chloride. Again insoluble white solid is removed by filtration. The crude product is chromatographed on silica gel (20:1 chloroform-methanol) to afford the product as a white solid (0.02 g). The NMR spectrum (in MeOH-$d_4$) shows a multiplet between 4.4 and 4.8, a multiplet between 3.2 and 3.4, complex absorptions between 2.2 and 2.7, and between 1.5 and 1.9, and a singlet at 1.2.

EXAMPLE 17

6-t-Butoxycarbonylamino-4-N-(carbo-t-butoxymethyl)-perhydro-1,4-thiazocin-5-one The above-named compound is prepared from 6-t-butoxycarbonylamino-perhydro-1,4-thiazocin-5-one (0.1 g) and t-butyl iodoacetate (0.2 g) according to the procedure described in Example 4. The product (0.05 g) is obtained after chromatography. The NMR spectrum is consistent with the assigned structure. A recrystallized sample (ether) analyzes for $C_{17}H_{30}N_2O_5S$.

EXAMPLE 18

4-N-(Carboxymethyl)-6-(1-carboethoxy-3-phenylpropylamino)-perhydro-1,4-thiazocin-S-one Removal of the t-butyl ester and t-butoxycarbonyl groups of 6-t-butoxycarbonylamino-4-N-(carbo-t-butoxymethyl)-perhydro-1,4-thiazocin-5-one with trifluoroacetic acid as in Example 5 followed by reductive condensation of this product with ethyl 2-keto-4-phenylbutyrate using sodium cyanoborohydride as in Example 6 affords, after chromatography, 4-N-(carboxymethyl)-6-(1-carboethoxy-3-phenylpropylamino)-perhydro-1,4-thiazocin-5-one.

EXAMPLE 19

By methods illustrated in the above examples, the keto acids and esters listed in Table I below can be reductively condensed using sodium cyanoborohydride with 6-amino-4-(1-carboxyethyl)-perhydro-1,4-thiazepin-5-one, 6-amino-4-carboxymethylperhydro-1,4-thiazepin-5-one or with their ethyl esters which can be prepared by standard Fisher esterification. Thusly obtained additional products of Formula I, after removal of protecting groups if any, are listed hereinbelow in Table II.

TABLE I
KETO ACIDS AND KETO ESTERS OF THE FORMULA: $R_1COCO_2R$ (a) Ph—$CH_2CH_2$—$COCO_2$—n-$C_4H_9$ (b) Ph—$CH_2CH_2COCO_2CH_2CH=CH_2$ (c) Ph—$CH_2CH_2CH_2$—$COCO_2C_2H_5$ (d) 4-Cl-Ph—$CH_2COCO_2H$ (e) (indol-3-yl)—$CH_2$—$COCO_2H$

TABLE I-continued
KETO ACIDS AND KETO ESTERS OF THE FORMULA: $R_1COCO_2R$ (f) 2-Cl-Ph—$CH_2CH_2COCO_2H$ (g) (indol-3-yl)—$CH_2CH_2$—$COCO_2C_2H_5$ (h) Ph—O—Ph—$CH_2CH_2COCO_2C_2H_5$ (i) 4-$CH_3O$-Ph—$CH_2CH_2COCO_2C_2H_5$ (j) 4-HO-Ph—$CH_2CH_2COCO_2CH_2C_6H_5$ (k) (naphth-2-yl)—$CH_2CH_2COCO_2CH_3$ (l) (naphth-1-yl)—$CH_2CH_2COCO_2C_2H_5$ (m) 3,4-diCl-Ph—$CH_2CH_2COCO_2C_2H_5$ (n) $(CH_3)_2CH$—$CH_2$—$COCO_2CH_3$ (o) $CH_3CH_2CH_2CH_2$—$COCO_2C_2H_5$ (p) 4-F-Ph—$CH_2CH_2COCO_2CH_3$ (q) $NH_2$—$(CH_2)_5$—$COCO_2H$  (1)

(r) 3-($CH_2NH_2$)-Ph—$CH_2CH_2COCO_2H$  (1)

TABLE I-continued
KETO ACIDS AND KETO ESTERS OF THE FORMULA: R₁COCO₂R (s) [imidazole]—CH₂CH₂COCO₂H  (2)

(t) [pyridine]—CH₂CH₂COCO₂H (u) [pyridine]—SCH₂C(=O)—COOH (v) HOCH₂CH₂—COCO₂C₂H₅  (3)

(w) (CH₃)₂N—(CH₂)₄—COCO₂H (x) [2-NO₂-phenyl]—CH₂CH₂COCO₂C₂H₅  (4)

(y) [2-NO₂-phenyl]—CH₂CH₂COCO₂H  (4)

(z) [isoquinolin-4-yl]—CH₂CH₂COCO₂H (aa) [isoquinolin-1-yl]—CH₂CH₂COCO₂H (bb) [thien-2-yl]—CH₂CH₂COCO₂C₂H₅

(cc) [quinolin-2-yl]—CH₂CH₂COCO₂H (dd) [phenyl]—OCH₂C(=O)—CO₂C₂H₅

(ee) [phenyl]—SCH₂C(=O)—CO₂H (ff) [phenyl]—CH₂SCH₂C(=O)—CO₂C₂H₅

(1) Protected as the N—phthaloyl derivative.
(2) 2-Imidazole NH protected as the N—benzyl derivative.
(3) Protected as the O—benzyl derivative.
(4) Precursor to m-amino derivative by H₂/Pd.

TABLE II
Additional Products of Formula I:

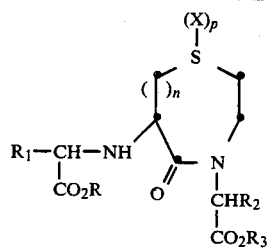

(n = 1; p = 0)

| | R | R₁ | R₂ | R₃ |
|---|---|---|---|---|
| (1) | n-C₄H₉— | [phenyl]—CH₂CH₂ | H | H |
| (2) | CH₂=CH—CH₂— | [phenyl]—CH₂CH₂ | H | C₂H₅ |

TABLE II-continued
Additional Products of Formula I:
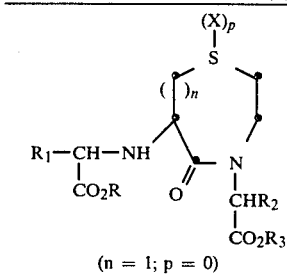
(n = 1; p = 0)
| | R | R₁ | R₂ | R₃ | |
|---|---|---|---|---|---|
| (3) | C₂H₅— | C₆H₅—CH₂CH₂ | H | C₂H₅ | |
| (4) | C₂H₅— | C₆H₅—CH₂CH₂ | H | CH₂=CH—CH₂ | (5) |
| (5) | C₆H₅—CH₂ | C₆H₅—CH₂CH₂ | H | H | |
| (6) | CH₃— | C₆H₅—CH₂CH₂ | H | n-C₄H₉— | (5) |
| (7) | H— | C₆H₅—CH₂CH₂ | H | C₆H₅— | (5) |
| (8) | CH₃— | C₆H₅—CH₂CH₂ | H | n-C₄H₉ | (5) |
| (9) | CH₃— | C₆H₅—CH₂CH₂ | H | C₂H₅— | |
| (10) | CH₃— | C₆H₅—CH₂CH₂ | H | C₆H₅—CH₂— | |
| (11) | H | C₆H₅—CH₂CH₂— | H | C₆H₅—CH₂— | |
| (12) | C₂H₅— | C₆H₅—CH₂CH₂CH₂ | H | H | |
| (13) | H | Cl—C₆H₄—CH₂— | H | H | |

TABLE II-continued

Additional Products of Formula I:

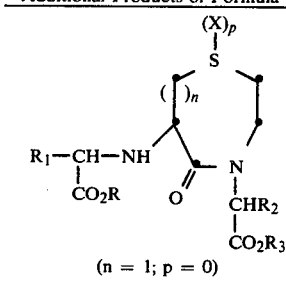

(n = 1; p = 0)

| | R | R₁ | R₂ | R₃ |
|---|---|---|---|---|
| (14) | H | indol-3-yl-CH₂— | H | H |
| (15) | H | (2-chlorophenyl)-CH₂CH₂— | H | H |
| (16) | $C_2H_5$— | indol-3-yl-CH₂CH₂— | H | $CH_3$ |
| (17) | $C_2H_5$— | (4-phenoxyphenyl)-CH₂CH₂— | H | H |
| (18) | $C_2H_5$— | (4-methoxyphenyl)-CH₂CH₂— | H | n-$C_4H_9$ |
| (19) | phenyl-CH₂— | (4-hydroxyphenyl)-CH₂CH₂— | H | H |
| (20) | $CH_3$— | (2-naphthyl)-CH₂CH₂— | H | $C_2H_5$ |
| (21) | $C_2H_5$ | (1-naphthyl)-CH₂CH₂— | H | phenyl-CH₂— |
| (22) | $C_2H_5$— | $CH_3S$—$CH_2CH_2$— | H | H |
| (23) | $CH_3$ | $(CH_3)_2$—CH—$CH_2$— | H | n-$C_4H_9$ |
| (24) | $C_2H_5$— | $CH_3CH_2CH_2CH_2$ | H | $C_2H_5$ |
| (25) | $CH_3$— | (4-fluorophenyl)-CH₂CH₂— | H | phenyl-CH₂— |
| (26) | H | $NH_2(CH_2)_5$— | H | H |

TABLE II-continued
Additional Products of Formula I:
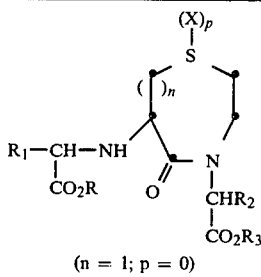
(n = 1; p = 0)
| | R | R₁ | R₂ | R₃ |
|---|---|---|---|---|
| (27) | H | 3-(aminomethyl)phenyl-CH₂CH₂— | H | H |
| (28) | H | (1H-imidazol-4-yl)-CH₂CH₂— | H | H |
| (29) | H | (pyridin-2-ylthio)CH₂— | H | H |
| (30) | C₂H₅ | HOCH₂CH₂— | H | C₂H₅ |
| (31) | H | (CH₃)₂N—(CH₂)₄— | H | H |
| (32) | C₂H₅ | 2,4-dichlorophenyl-CH₂CH₂— | S | C₆H₅CH₂ |
| (33) | H | 2-aminophenyl-CH₂CH₂— | H | C₆H₅CH₂— |
| (34) | H | isoquinolin-4-yl-CH₂CH₂ | H | H |
| (35) | H | pyridin-4-yl-CH₂CH₂ | H | H |
| (36) | C₂H₅ | 2-aminophenyl-CH₂CH₂— | H | H |

TABLE II-continued
Additional Products of Formula I:
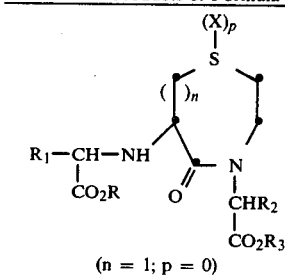
(n = 1; p = 0)
| | R | R₁ | R₂ | R₃ | |
|---|---|---|---|---|---|
| (37) | $C_2H_5$ | 1-(CH₂CH₂)-isoquinoline | H | $C_2H_5$ | |
| (38) | $C_2H_5$ | 3-(CH₂CH₂)-thiophene | S | $CH_2=CH-CH_2$ | |
| (39) | H | 2-(CH₂CH₂)-quinoline | H | H | |
| (40) | $C_2H_5$ | $C_6H_5-O-CH_2$ | H | H | |
| (41) | H | $C_6H_5-S-CH_2$ | H | H | |
| (42) | $C_2H_5$ | $C_6H_5-CH_2SCH_2$ | H | H | |
| (43) | n-$C_4H_9-$ | $C_6H_5-CH_2CH_2$ | $-CH_3$ | H | |
| (44) | $CH_2=CH-CH_2-$ | $C_6H_5-CH_2CH_2$ | $-CH_3$ | $C_2H_5$ | |
| (45) | $C_2H_5-$ | $C_6H_5-CH_2CH_2$ | $-CH_3$ | $C_2H_5$ | |
| (46) | $C_2H_5-$ | $C_6H_5-CH_2CH_2$ | $-CH_3$ | $CH_2=CH-CH_2$ | (5) |
| (47) | $C_6H_5-CH_2$ | $C_6H_5-CH_2CH_2$ | $-CH_3$ | H | |

TABLE II-continued
Additional Products of Formula I:
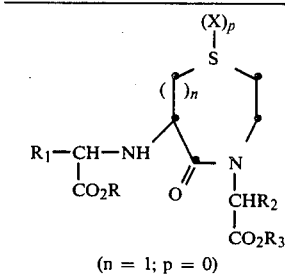
(n = 1; p = 0)
| | R | R₁ | R₂ | R₃ | |
|---|---|---|---|---|---|
| (48) | $CH_3-$ | phenyl-$CH_2CH_2$ | $-CH_3$ | n-$C_4H_9-$ | (5) |
| (49) | $H-$ | phenyl-$CH_2CH_2$ | $-CH_3$ | phenyl | (5) |
| (50) | $CH_3-$ | phenyl-$CH_2CH_2$ | $-CH_3$ | n-$C_4H_9$ | (5) |
| (51) | $CH_3-$ | phenyl-$CH_2CH_2$ | $-CH_3$ | $C_2H_5-$ | |
| (52) | $CH_3-$ | phenyl-$CH_2CH_2$ | $-CH_3$ | phenyl-$CH_2-$ | |
| (53) | $H$ | phenyl-$CH_2CH_2-$ | $-CH_3$ | phenyl-$CH_2-$ | |
| (54) | $C_2H_5-$ | phenyl-$CH_2CH_2CH_2$ | $-CH_3$ | H | |
| (55) | $H$ | 4-Cl-phenyl-$CH_2-$ | $-CH_3$ | H | |
| (56) | $H$ | (1H-indol-3-yl)-$CH_2$ | $-CH_3$ | H | |
| (57) | $H$ | 2-Cl-phenyl-$CH_2CH_2$ | $-CH_3$ | H | |

TABLE II-continued

Additional Products of Formula I:

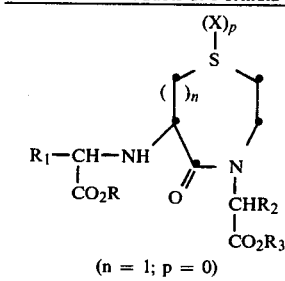

(n = 1; p = 0)

| | R | R₁ | R₂ | R₃ |
|---|---|---|---|---|
| (58) | $C_2H_5-$ | 3-indolyl-$CH_2CH_2-$ | $-CH_3$ | $CH_3$ |
| (59) | $C_2H_5-$ | 4-phenoxyphenyl-$CH_2CH_2-$ | $CH_3$ | H |
| (60) | $C_2H_5-$ | 4-methoxyphenyl-$CH_2CH_2-$ | $CH_3$ | $n-C_4H_9$ |
| (61) | benzyl | 4-hydroxyphenyl-$CH_2CH_2-$ | $CH_3$ | H |
| (62) | $CH_3-$ | 2-naphthyl-$CH_2CH_2-$ | $CH_3$ | $C_2H_5$ |
| (63) | $C_2H_5$ | 1-naphthyl-$CH_2CH_2-$ | $CH_3$ | benzyl |
| (64) | $C_2H_5-$ | $CH_3S-CH_2CH_2-$ | $CH_3$ | H |
| (65) | $CH_3$ | $(CH_3)_2-CH-CH_2-$ | $CH_3$ | $n-C_4H_9$ |
| (66) | $C_2H_5-$ | $CH_3CH_2CH_2CH_2$ | $CH_3$ | $C_2H_5$ |
| (67) | $CH_3-$ | 4-fluorophenyl-$CH_2CH_2-$ | $CH_3$ | benzyl |
| (68) | H | $NH_2(CH_2)_5-$ | $CH_3$ | H |
| (69) | H | 2-(aminomethyl)phenyl-$CH_2CH_2-$ | $CH_3$ | H |
| (70) | H | 4-imidazolyl-$CH_2CH_2-$ | $CH_3$ | H |

TABLE II-continued

Additional Products of Formula I:

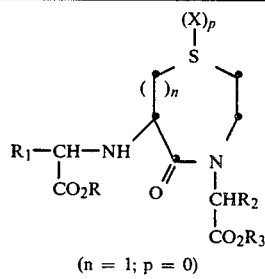

(n = 1; p = 0)

| | R | R₁ | R₂ | R₃ |
|---|---|---|---|---|
| (71) | H | 2-(methylthiomethyl)pyridine: N-pyridyl-SCH₂- | CH₃ | H |
| (72) | C₂H₅ | HOCH₂CH₂— | CH₃ | C₂H₅ |
| (73) | H | (CH₃)₂N—(CH₂)₄— | CH₃ | H |
| (74) | C₂H₅ | 2,4-dichlorophenyl-CH₂CH₂— | CH₃ | C₆H₅CH₂ |
| (75) | H | 2-aminophenyl-CH₂CH₂— | CH₃ | C₆H₅CH₂— |
| (76) | H | isoquinolin-4-yl-CH₂CH₂— | CH₃ | H |
| (77) | H | pyridin-4-yl-CH₂CH₂— | CH₃ | H |
| (78) | C₂H₅ | 2-aminophenyl-CH₂CH₂— | CH₃ | H |
| (79) | C₂H₅ | isoquinolin-1-yl-CH₂CH₂— | CH₃ | C₂H₅ |
| (80) | C₂H₅ | thien-2-yl-CH₂CH₂— | CH₃ | CH₂=CH—CH₂ |

TABLE II-continued

Additional Products of Formula I:

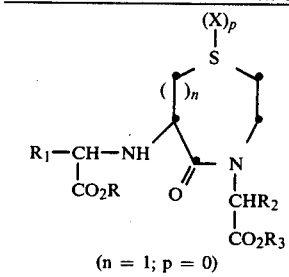

(n = 1; p = 0)

| | R | R₁ | R₂ | R₃ |
|---|---|---|---|---|
| (81) | H | quinolin-2-yl-CH₂CH₂ | CH₃ | H |
| (82) | C₂H₅ | C₆H₅—O—CH₂ | CH₃ | H |
| (83) | H | C₆H₅—S—CH₂ | CH₃ | H |
| (84) | C₂H₅ | C₆H₅—CH₂SCH₂ | CH₃ | H |

(5) The required R₂ ester can be prepared by first protecting VIII as its t-BOC derivative and then reacting it with DCC and the desired alcohol or phenol in the presence of 4-dimethylamino pyridine. In some examples, the R₂ ester can also be introduced by reaction of protected VIII with cesium carbonate and the appropriate alkyl halide in DMF.

What is claimed is:

1. A compound of the formula:

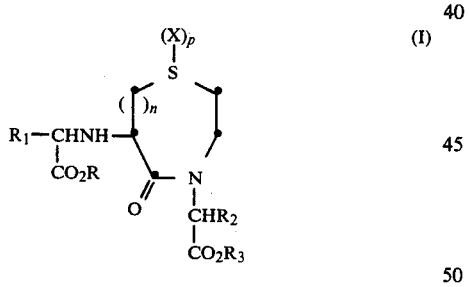
(I)

wherein

R and $R_3$ are independently hydrogen, $C_1$–$C_6$ alkyl, aryl, and aralkyl;

$R_1$ is hydrogen; hydrocarbon of from 1 to 12 carbon atoms which include branched, cyclic and unsaturated hydrocarbon groups; substituted $C_1$–$C_6$ alkyl wherein the substituent can be halo, hydroxy, carboxy, lower alkylthio, lower alkoxy, lower alkoxy carbonyl, lower aralkoxy carbonyl, amino, lower alkylamino, diloweralkylamino, or acylamino; substituted $C_1$–$C_6$ alkyl having the formula $R_A(CH_2)_n$—Q—$(CH_2)_m$ wherein n is 0-2, m is 1-3, $R_A$ is aryl or heteroaryl optionally substituted by amino, diloweralkylamino, lower alkylamino, hydroxy, hydroxy loweralkyl, aminoloweralkyl, trihaloloweralkyl, cyano, nitro, sulfonamido, aroyl, lower alkyl, halo, dihalo, and lower alkoxy, and Q is O, S, N—$R_B$, CONR$_C$, NR$_C$CO, CH=CH wherein $R_B$ is hydrogen, loweralkyl, aryl, aralkyl, lower alkanoyl, or aroyl, and $R_C$ is hydrogen or lower alkyl; aryl; substituted aryl wherein the substituent is lower alkyl, amino loweralkyl, loweralkoxy, aryloxy, aroyl, hydroxy, halo, or dihalo; aralkyl or heteroaralkyl which include branched lower alkyl groups; substituted aralkyl or substituted heteroaralkyl which include branched lower alkyl groups wherein the lower alkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, amino lower alkyl, lower alkanoylamino, aroylamino, diloweralkylamino, lower alkylamino, hydroxy loweralkyl, trihalo loweralkyl, nitro, cyano, or sulfonamido;

$R_2$ is hydrogen or loweralkyl;

n is 1 or 2;

p is 0 or 1;

X is oxygen; and, the pharmaceutically acceptable salts thereof, wherein in said R–$R_3$ groups, unless otherwise stated, the loweralkyl groups contain from one to six carbon atoms; aryl and the prefix "ar" represent phenyl, naphthyl or biphenyl; the aralkyl and heteroaralkyl groups contain from one to six carbon atoms in the alkyl portion thereof and represent benzyl, phenethyl, 3,3-diphenylpropyl, or 3-indolylmethyl; heteroaryl represents indolyl, thienyl, imidazolyl, furyl, benzimidazolyl, pyridyl, quinolinyl, isoquinolinyl, and benzothienyl; aroyl denotes benzoyl or 1-naphthoyl; acylamino denotes loweralkanoylamino and aroylamino which are selected from the group consisting of acetylamino, and benzoylamino; and, alkoxy denotes a loweralkyl group bonded to oxygen.

2. A compound of claim 1 wherein:

R and $R_3$ are hydrogen, loweralkyl, aryl or aralkyl;

$R_1$ is a hydrocarbon of 1-10 carbon atoms which include branched, cyclic and unsaturated hydrocarbon groups; substituted loweralkyl wherein the substituent can be hydroxy, lower alkylthio, amino, alkylamino, diloweralkylamino, and acylamino; substituted lower alkyl having the formula $R_A(CH_2)_n—Q—(CH_2)_m—$ wherein n is 0-2, m is 1-3, $R_A$ is aryl or heteroaryl optionally substituted by alkyl, halo, dihalo, amino, cyano, hydroxy, or alkoxy, and Q is O, S, N—$R_B$, $CONR_C$, $NR_CCO$, or CH=CH wherein $R_B$ is hydrogen, lower alkyl, aralkyl, lower alkanoyl, or aroyl and R is hydrogen or lower alkyl; aralkyl or heteroaralkyl which include branched lower alkyl groups;

$R_2$ is hydrogen or lower alkyl;

n is 1 or 2; and, p is 0.

3. A compound of claim 2 wherein n is 1.

4. A compound of claim 3 wherein:

R and $R_3$ are independently hydrogen, lower alkyl of 1 to 4 carbon atoms, phenyl, or benzyl;

$R_2$ is hydrogen or lower alkyl $R_1$ is alkyl of 1-8 carbon atoms which include branched alkyl groups; substituted lower alkyl wherein the substituent can be amino or loweralkylthio; substituted lower alkyl having the formula $R_A(CH_2)_n—Q—(CH_2)_m—$ wherein n is O, m is 1, $R_A$ is phenyl, and Q is O or S; aralkyl wherein the aryl is phenyl or naphthyl and the alkyl group contains 1 to 3 carbon atoms, or heteroaralkyl wherein the heteroaryl group is indole, thiophene, imidazole, pyridine, quinoline or isoquinoline and the alkyl group contains 1 to 3 carbon atoms; substituted aralkyl wherein the aryl is phenyl, the alkyl contains 1 to 3 carbon atoms, and the substituents can be halo, hydroxy, phenoxy, lower alkoxy, amino, or aminomethyl, and, $R_2$ is hydrogen, loweralkyl.

5. A compound which has the formula:

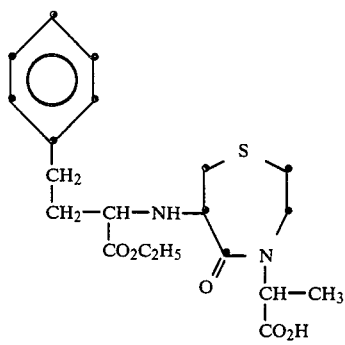

6. The compound of claim 5 which is: 4-N-(1(S)-carboxyethyl)-6(R)-(1(S)-carboethoxy-3-phenylpropylamino)perhydro-1,4-thiazepin-5-one.

7. A compound which has the formula:

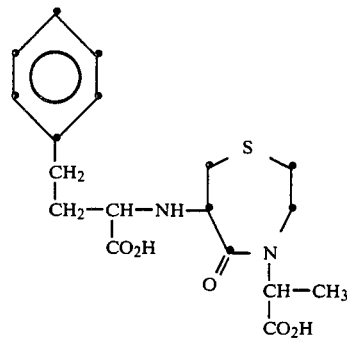

8. The compound of claim 7 which is: 4-N-(1(S)-carboxyethyl)-6(R)-(1(S)-carboxy-3-phenylpropylamino)-perhydro-1,4-thiazepin-5-one.

9. A compound which has the formula:

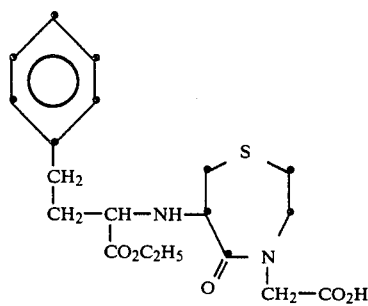

10. The compound of claim 9 which is: 4-N-carboxymethyl-6(R)-(1(S)-carboethoxy-3-phenylpropylamino)perhydro-1,4-thiazepin-5-one.

11. A compound which has the formula:

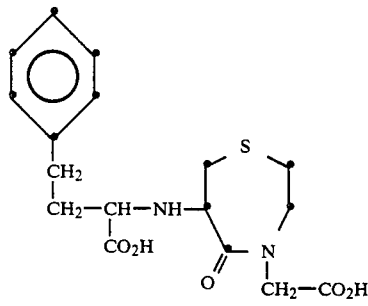

12. The compound of claim 11 which is: 4-N-carboxymethyl-6(R)-(1(S)-carboxy-3-phenylpropylamino)perhydro-1,4-thiazepin-5-one.

13. A pharmaceutical composition useful in the treatment of hypertension which comprises a pharmaceutically acceptable carrier and an antihypertensively effective amount of a compound of the formula:

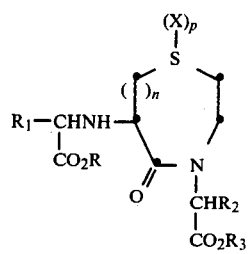

wherein
- R and $R_3$ are independently hydrogen, $C_1$–$C_6$ alkyl, aryl, and aralkyl;
- $R_1$ is hydrogen; hydrocarbon of from 1 to 12 carbon atoms which include branched, cyclic and straight chain hydrocarbon groups; substituted $C_1$–$C_6$ alkyl wherein the substituent can be halo, hydroxy, carboxy, lower alkylthio, lower alkoxy, lower alkoxy carbonyl, lower aralkoxy carbonyl, amino, lower alkylamino, diloweralkylamino, or acylamino; substituted $C_1$–$C_6$ alkyl having the formula $R_A(CH_2)_n$—Q—$(CH_2)_m$ wherein n is 0–2, m is 1–3, $R_A$ is aryl or heteroaryl optionally substituted by amino, diloweralkylamino, lower alkylamino, hydroxy, hydroxy loweralkyl, aminoloweralkyl, trihaloloweralkyl, cyano, nitro, sulfonamido, aroyl, lower alkyl, halo, dihalo, and lower alkoxy, and Q is O, S, N—$R_B$, $CONR_C$, $NR_CCO$, CH=CH wherein $R_B$ is hydrogen, loweralkyl, aryl, aralkyl, lower alkanoyl, or aroyl, and $R_C$ is hydrogen or lower alkyl; aryl; substituted aryl wherein the substituent is lower alkyl, amino loweralkyl, loweralkoxy, aryloxy, aroyl, hydroxy, halo, or dihalo; aralkyl or heteroaralkyl which include branched lower alkyl groups; substituted aralkyl or substituted heteroaralkyl which include branched lower alkyl groups wherein the lower alkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, amino lower alkyl, lower alkanoylamino, aroylamino, diloweralkylamino, lower alkylamino, hydroxy loweralkyl, trihalo loweralkyl, nitro, cyano, or sulfonamido;
- $R_2$ is hydrogen or loweralkyl;
- n is 1 or 2;
- p is — or 1;
- X is oxygen; and, the pharmaceutically acceptable salts thereof, wherein in said R–$R_3$ groups, unless otherwise stated, the loweralkyl groups contain from one to six carbon atoms; aryl and the prefix "ar" represent phenyl, naphthyl or biphenyl; the aralkyl and heteroaralkyl groups contain from one to six carbon atoms in the alkyl portion thereof and represent benzyl, phenethyl, 3,3-diphenylpropyl, or 3-indolylmethyl; heteroaryl represents indolyl, thienyl, imidazolyl, furyl, benzimidazolyl, pyridyl, quinolinyl, isoquinolinyl, and benzothienyl; aroyl denotes benzoyl or 1-naphthoyl; acylamino denotes loweralkanoylamino and aroylamino which are selected from the group consisting of acetylamino, and benzoylamino; and, alkoxy denotes a loweralkyl group bonded to oxygen.

14. The composition of claim 13 wherein said compound is a member of the group:
4-N-(1(S)-carboxyethyl)-6(R)-(1(S)-carboethoxy-3-phenylpropylamino)perhydro-1,4-thiazepin-5-one;
4-N-(1(S)-carboxyethyl)-6(R)-(1(S)-carboxy-3-phenylpropylamino)perhydro-1,4-thiazepin-5-one;
4-N-carboxymethyl-6(R)-(1(S)-carboethoxy-3-phenylpropylamino)perhydro-1,4-thiazepin-5-one; and, 4-N-carboxymethyl-6(R)-(1(S)-carboxy-3-phenylpropylamino)perhydro-1,4-thiazepin-5-one.

15. A pharmaceutical composition useful in the treatment of hypertension which comprises a pharmaceutically acceptable carrier; an antihypertensively effective amount of a compound of the formula:

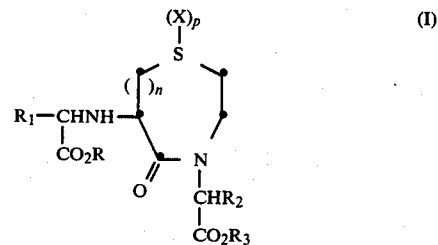

wherein:
- R and $R_3$ are independently hydrogen, $C_1$–$C_6$ alkyl, aryl, and aralkyl;
- $R_1$ is hydrogen; hydrocarbon of from 1 to 12 carbon atoms which include branched, cyclic and straight chain hydrocarbon groups; substituted $C_1$–$C_6$ alkyl wherein the substituent can be halo, hydroxy, carboxy, lower alkylthio, lower alkoxy, lower alkoxy carbonyl, lower aralkoxy carbonyl, amino, lower alkylamino, diloweralkylamino, or acylamino; substituted $C_1$–$C_6$ alkyl having the formula $R_A(CH_2)_n$—Q—$(CH_2)_m$ wherein n is 0–2, m is 1–3, $R_A$ is aryl or heteroaryl optionally substituted by amino, diloweralkylamino, lower alkylamino, hydroxy, hydroxy loweralkyl, aminoloweralkyl, trihaloloweralkyl, cyano, nitro, sulfonamido, aroyl, lower alkyl, halo, dihalo, and lower alkoxy, and Q is O, S, N—$R_B$, $CONR_C$, $NR_CCO$, CH=CH wherein $R_B$ is hydrogen, loweralkyl, aryl, aralkyl, lower alkanoyl, or aroyl, and $R_C$ is hydrogen or lower alkyl; aryl; substituted aryl wherein the substituent is lower alkyl, amino loweralkyl, loweralkoxy, aryloxy, aroyl, hydroxy, halo, or dihalo; aralkyl or heteroaralkyl which include branched lower alkyl groups; substituted aralkyl or substituted heteroaralkyl which include branched lower alkyl groups wherein the lower alkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, amino lower alkyl, lower alkanoylamino, aroylamino, diloweralkylamino, lower alkylamino, hydroxy loweralkyl, trihalo loweralkyl, nitro, cyano, or sulfonamido;
- $R_2$ is hydrogen or loweralkyl;
- n is 1 or 2;
- p is 0 or 1;
- X is oxygen; or, the pharmaceutically acceptable salts thereof; wherein in said R–$R_3$ groups, unless otherwise stated, the loweralkyl groups contain from one to six carbon atoms; aryl and the prefix "ar" represent phenyl, naphthyl or biphenyl; the aralkyl and heteroaralkyl groups contain from one to six carbon atoms in the alkyl portion thereof and represent benzyl, phenethyl, 3,3-diphenylpropyl, or 3-indolylmethyl; heteroaryl represents indolyl, thienyl, imidazolyl, furyl, benzimidazolyl, pyridyl, quinolinyl, isoquinolinyl, and benzothienyl; aroyl denotes benzoyl or 1-naphthoyl; acylamino denotes loweralkanoylamino and aroylamino which are selected from the group consisting of acetylamino, and benzoylamino; and, alkoxy denotes a loweralkyl group bonded to oxygen, and, an antihypertensive and/or diuretic compound selected from the group consisting of hydrochlorothiazide, methyldopa, timolol, the pivaloyloxyethyl ester of methyldopa, indacrinone and variable ratios of its enantiomers, (+)-4-{3-[2-(1-hydroxycyclohexyl)ethyl]-4-oxo-2-thiazolidinyl}propyl}benzoic acid, as well as admixtures and combinations thereof.

16. The composition of claim 15 wherein said pharmaceutically effective compound is a member of the group:
4-N-(1(S)-carboxyethyl)-6(R)-(1(S)-carboethoxy-3-phenylpropylamino)perhydro-1,4-thiazepin-5-one;
4-N-(1(S)-carboxyethyl)-6(R)-(1(S)-carboxy-3-phenylpropylamino)perhydro-1,4-thiazepin-5-one;
4-N-carboxymethyl-6(R)-(1(S)-carboethoxy-3-phenylpropylamino)perhydro-1,4-thiazepin-5-one; and, 4-N-carboxymethyl-6(R)-(1(S)-carboxy-3-phenylpropylamino)perhydro-1,4-thiazepin-5-one.

17. A method for treating hypertension which comprises administering to a patient in need of such treatment an antihypertensively effective amount of a compound of the formula:

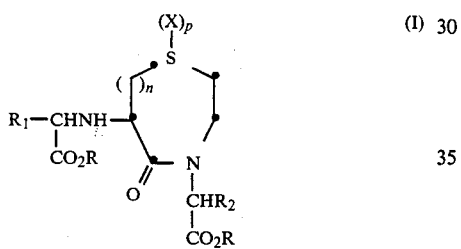

wherein:
R and $R_3$ are independently hydrogen, $C_1$-$C_6$ alkyl, aryl, and aralkyl;
$R_1$ is hydrogen; hydrocarbon of from 1 to 12 carbon atoms which include branched, cyclic and straight chain hydrocarbon groups; substituted $C_1$-$C_6$ alkyl wherein the substituent can be halo, hydroxy, carboxy, lower alkylthio, lower alkoxy, lower alkoxy carbonyl, lower aralkoxy carbonyl, amino, lower alkylamino, diloweralkylamino, or acylamino; substituted $C_1$-$C_6$ alkyl having the formula $R_A(CH_2)_n$—Q—$(CH_2)_m$ wherein n is 0–2, m is 1–3, $R_A$ is aryl or heteroaryl optionally substituted by amino, diloweralkylamino, lower alkylamino, hydroxy, hydroxy loweralkyl, aminoloweralkyl, trihaloloweralkyl, cyano, nitro, sulfonamido, aroyl, lower alkyl, halo, dihalo, and lower alkoxy, and Q is O, S, N—$R_B$, CONR$_C$, NR$_C$CO, CH=CH wherein $R_B$ is hydrogen, loweralkyl, aryl, aralkyl, lower alkanoyl, or aroyl, and $R_C$ is hydrogen or lower alkyl; aryl; substituted aryl wherein the substituent is lower alkyl, amino loweralkyl, loweralkoxy, aryloxy, aroyl, hydroxy, halo, or dihalo; aralkyl or heteroaralkyl which include branched lower alkyl groups; substituted aralkyl or substituted heteroaralkyl which include branched lower alkyl groups wherein the lower alkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, amino lower alkyl, lower alkanoylamino, aroylamino, diloweralkylamino, lower alkylamino, hydroxy loweralkyl, trihalo loweralkyl, nitro, cyano, or sulfonamido;
$R_2$ is hydrogen or loweralkyl;
n is 1 or 2;
p is 0 or 1;
X is oxygen; and,
the pharmaceutically acceptable salts thereof, wherein in said R–$R_3$ groups, unless otherwise stated, the loweralkyl groups contain from one to six carbon atoms; aryl and the prefix "ar" represent phenyl, naphthyl or biphenyl; the aralkyl and heteroaralkyl groups contain from one to six carbon atoms in the alkyl portion thereof and represent benzyl, phenethyl, 3,3-diphenylpropyl, or 3-indolylmethyl; heteroaryl represents indolyl, thienyl, imidazolyl, furyl, benzimidazolyl, pyridyl, quinolinyl, isoquinolinyl, and benzothienyl; aroyl denotes benzoyl or 1-naphthoyl; acylamino denotes loweralkanoylamino and aroylamino which are selected from the group consisting of acetylamino, and benzoylamino; and, alkoxy denotes a loweralkyl group bonded to oxygen.

18. The method of claim 17 wherein said compound is a member of the group:
4-N-(1(S)-carboxyethyl)-6(R)-(1(S)-carboethoxy-3-phenylpropylamino)perhydro-1,4-thiazepin-5-one;
4-N-(1(S)-carboxyethyl)-6(R)-(1(S)-carboxy-3-phenylpropylamino)perhydro-1,4-thiazepin-5-one;
4-N-carboxymethyl-6(R)-(1(S)-carboethoxy-3-phenylpropylamino)perhydro- 1,4-thiazepin-5-one; and, 4-N-carboxymethyl-6(R)-(1(S)-carboxy-3-phenylpropylamino)perhydro-1,4-thiazepin-5-one.

19. A process for producing a compound having the formula:

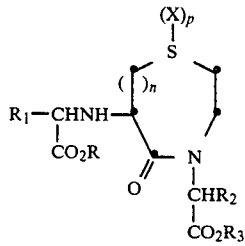

wherein R, $R_1$, $R_2$, $R_3$, X, n and p are as defined in claim 1, which process comprises: reductively condensing an α-ketoacid or α-ketoester having the formula $R_1$CO—CO$_2$R wherein R and $R_1$ are as defined in claim 1 with an α-aminothialactam of the formula:

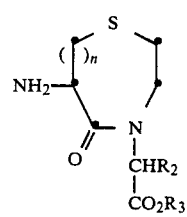

wherein $R_2$, $R_3$ and n are as defined in claim 1, to afford, after optionally reacting with a peracid followed by removal of protecting groups, if necessary, the desired product and, if desired, isolating the biologically more active isomer by chromatography or fractional crystallization and, if further desired, preparing a salt thereof by conventional means.

20. The process of claim 19 wherein p is 0 and n is 1.

* * * * *